United States Patent [19]

Stenberg et al.

[11] 4,272,373
[45] Jun. 9, 1981

[54] APPARATUS FOR THE TRANSFER OF SUBSTANCES BETWEEN TWO FLUIDS WITH SIMULTANEOUS TEMPERING OF AT LEAST ONE OF THE FLUIDS

[75] Inventors: Kaj O. Stenberg, Staffanstorp; Lars J. C. Traven, Lund, both of Sweden

[73] Assignee: Gambro AB, Sweden

[21] Appl. No.: 6,250

[22] Filed: Jan. 24, 1979

[30] Foreign Application Priority Data

Feb. 2, 1978 [SE] Sweden .............................. 7801230

[51] Int. Cl.³ ........................ B01D 31/00; A61M 1/03
[52] U.S. Cl. .................................... 210/175; 210/456;
210/321.3; 165/101; 422/48; 422/46;
261/DIG. 28
[58] Field of Search ...................... 422/45, 46, 47, 48;
210/23 R, 150, 175, 180, 181, 188, 307, 321 B,
335, 456; 128/DIG. 3; 55/16, 158; 165/100,
101; 261/DIG. 28

[56] References Cited

U.S. PATENT DOCUMENTS

| | | | |
|---|---|---|---|
| 3,037,504 | 6/1962 | Everett | 422/45 |
| 3,212,498 | 10/1965 | McKirdy et al. | 210/321 B |
| 3,332,746 | 7/1967 | Claff et al. | 422/48 |
| 3,398,091 | 8/1968 | Greatorex | 210/321 R |
| 3,413,095 | 11/1968 | Bramson | 422/48 |
| 3,484,211 | 12/1969 | Mon et al. | 422/48 |
| 3,488,158 | 1/1970 | Bentley et al. | 422/47 |
| 3,493,347 | 2/1970 | Everett | 422/45 |
| 3,515,275 | 6/1970 | Bowman | 210/22 |
| 3,560,377 | 2/1971 | Loeffler | 210/321 R |
| 3,594,130 | 7/1971 | North, Jr. | 422/48 |
| 3,631,986 | 1/1972 | Sausse | 210/321 B |
| 3,684,097 | 8/1972 | Mathewson, Jr. et al. | 210/321 B |
| 3,768,977 | 10/1973 | Brumfield et al. | 422/46 |
| 3,856,475 | 12/1974 | Marx | 422/45 |
| 3,998,593 | 12/1976 | Yoshida et al. | 422/48 |

FOREIGN PATENT DOCUMENTS 1447174 8/1976 United Kingdom ...................... 422/45
1470428 4/1977 United Kingdom ...................... 422/45

OTHER PUBLICATIONS

"Clinical Evaluation of Harvey H200 . . . Oxygenator", Page et al., Journal of Thoracic and Card. Sur., vol. 67 #2, Feb. 1974.
"Heart Surgery with a Membrane Oxygenator in Infants", Sugg et al., Journ. of Thor. and Card. Surgery, vol. 67 #4, Apr. 1974.
"The Infant Temptrol Oxygenator", Clark et al., Journ. of Thoracic and Cardiovascular Surgery, vol. 60 #1, 1970.

Primary Examiner—Charles N. Hart
Assistant Examiner—David R. Sadowski
Attorney, Agent, or Firm—Lerner, David, Littenberg & Samuel

[57] ABSTRACT

Apparatus for the transfer of substances between two fluids with the simultaneous tempering of at least one of the fluids. The apparatus includes at least one heat permeable membrane having first and second opposing surfaces for the transfer of heat therethrough. First and second fluid conducting means are provided for conducting a first and second fluid, respectively. Transfer means are provided for transferring substances between the first and second fluids. The second fluid conducting means conducts the second fluid along the first surface of the heat permeable membrane and third fluid conducting means are providing for conducting a third fluid along the second surface of the heat permeable membrane for tempering the second fluid. According to the preferred embodiment, the transfer means may comprise either means for directly mixing the first fluid into the second fluid or may comprise a semipermeable membrane for diffusing substances therethrough between the first and second fluids.

24 Claims, 22 Drawing Figures

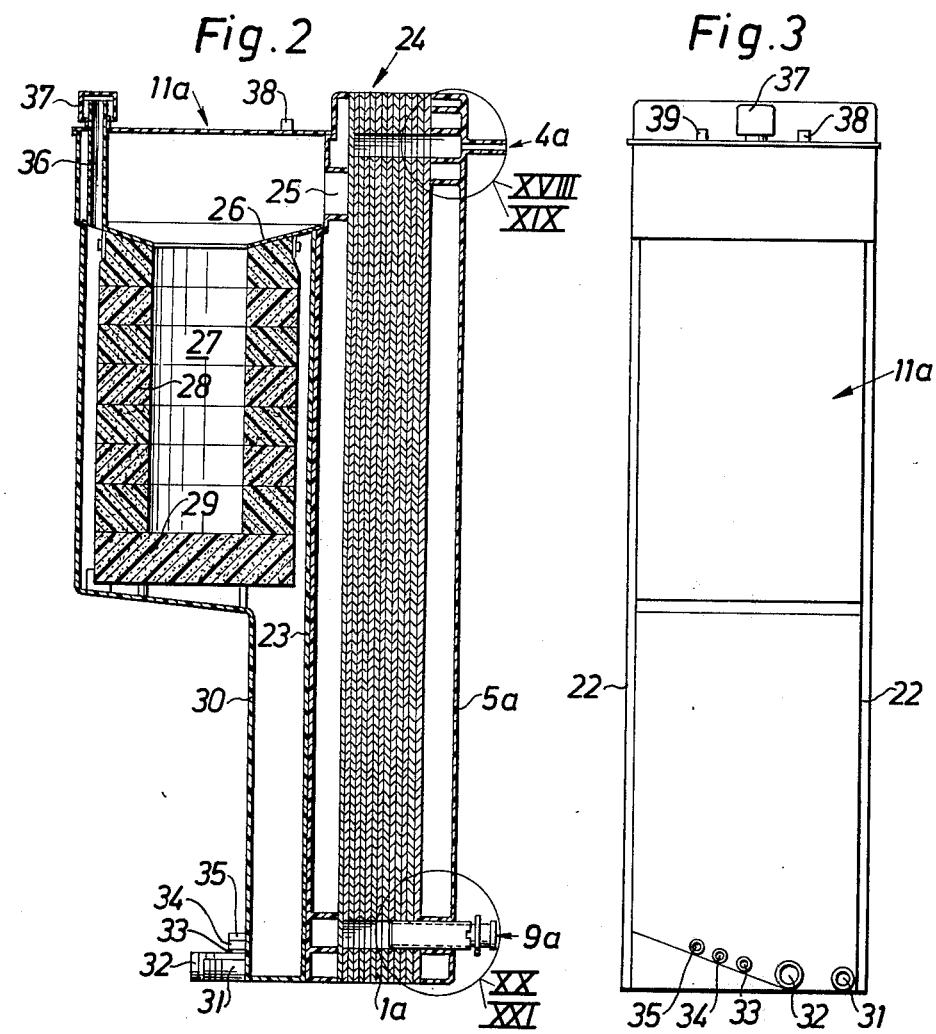
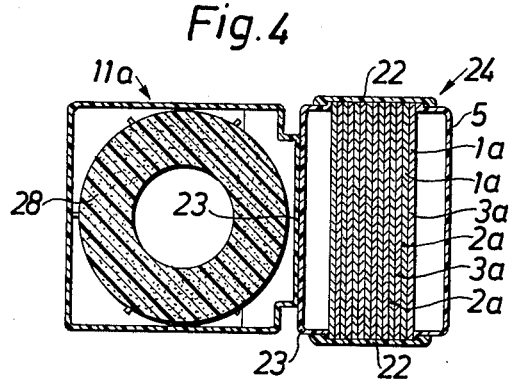

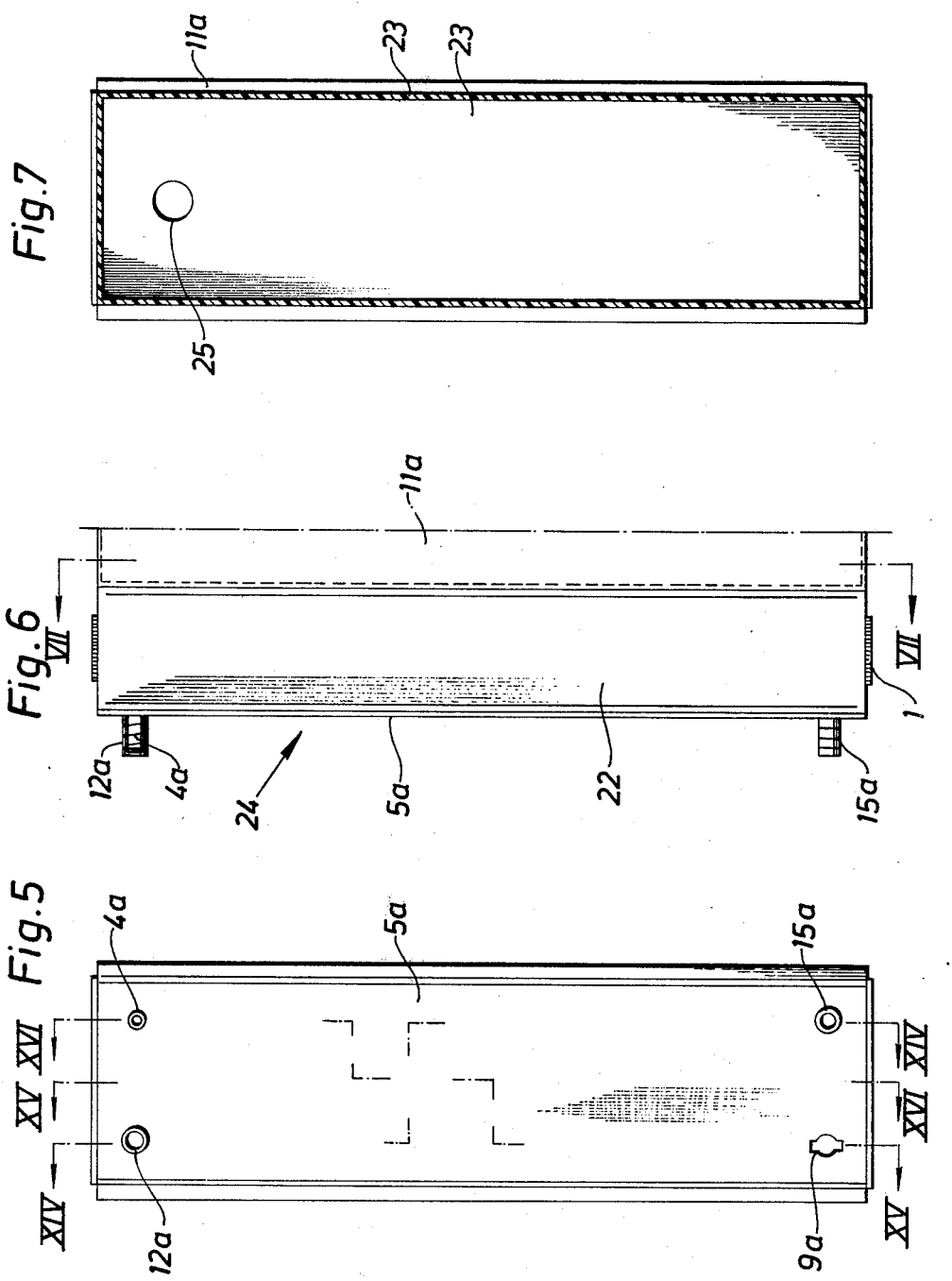

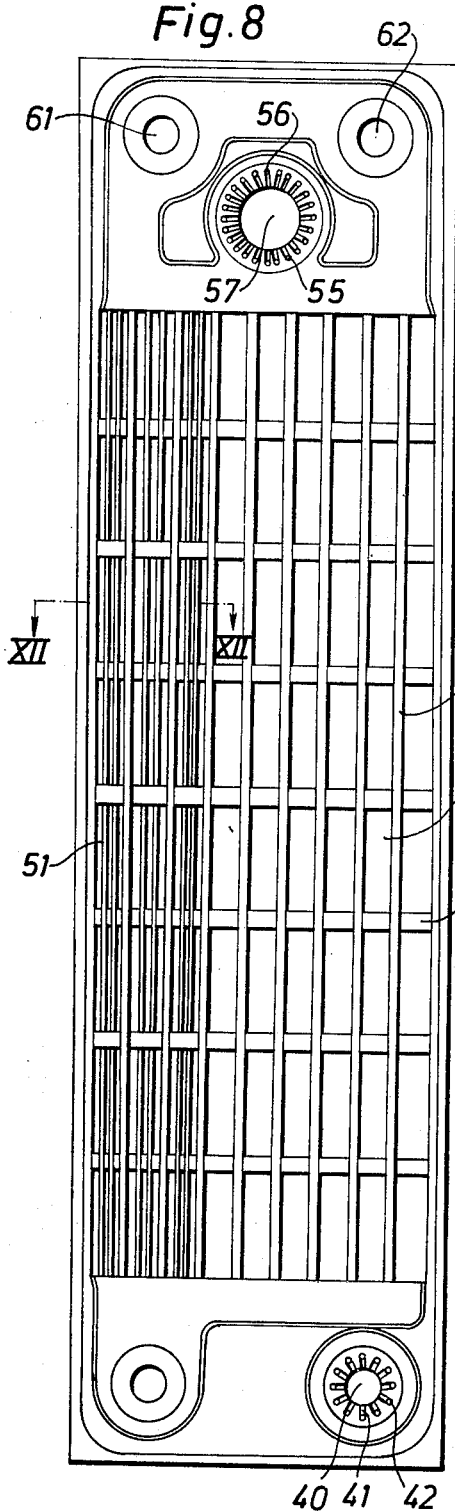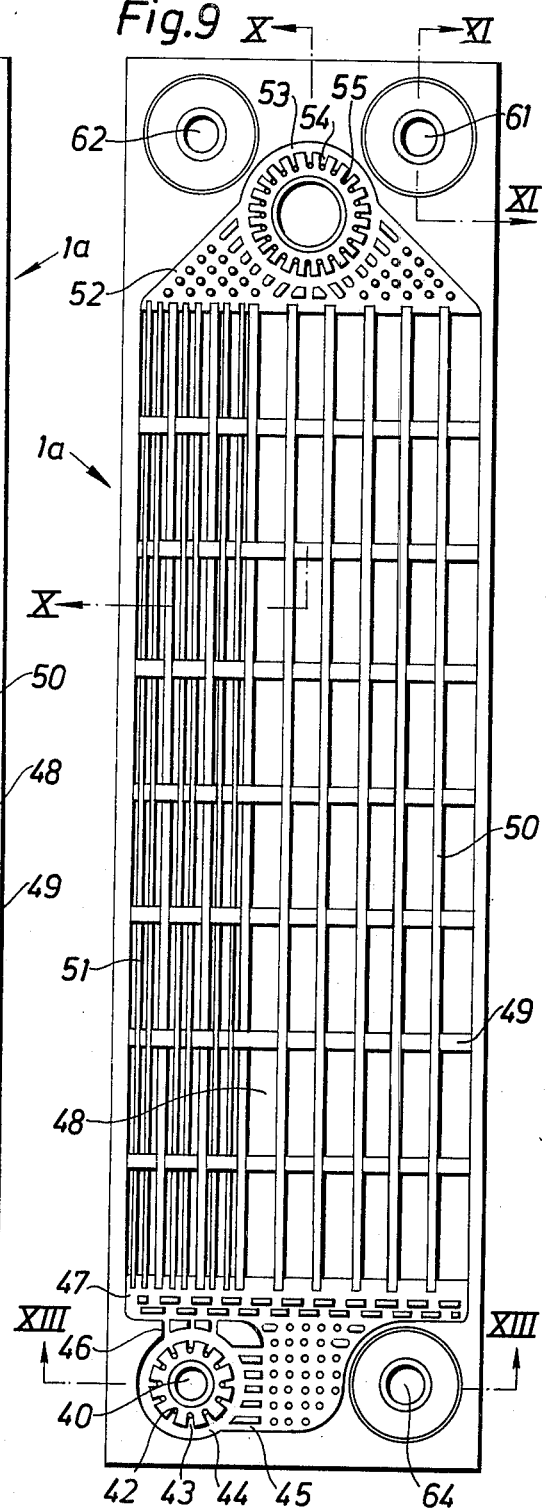
Fig.8
Fig.9

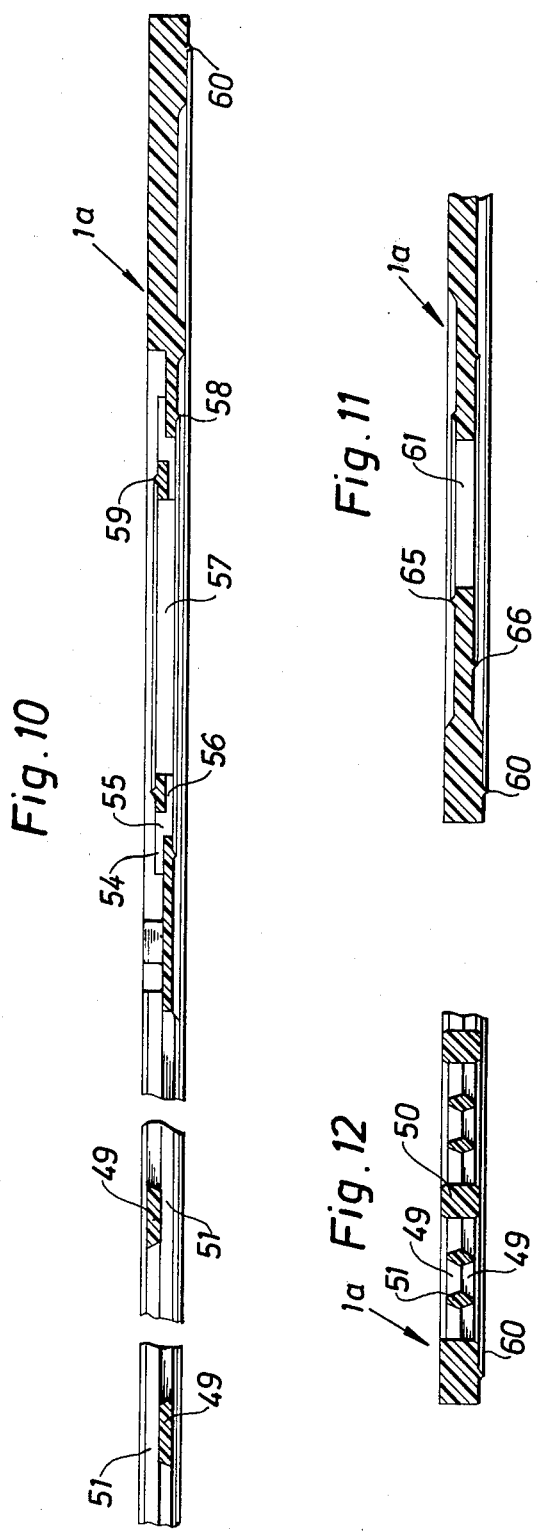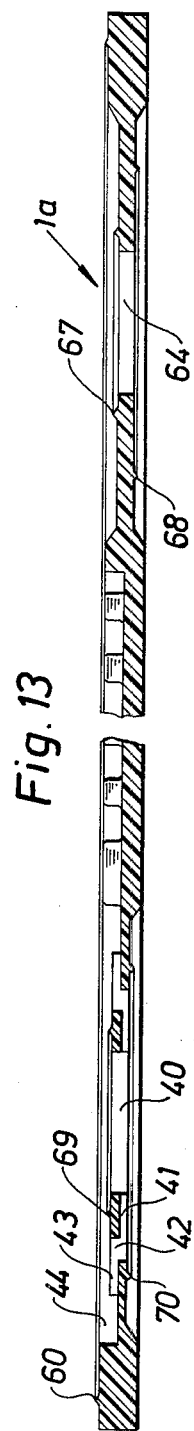

APPARATUS FOR THE TRANSFER OF SUBSTANCES BETWEEN TWO FLUIDS WITH SIMULTANEOUS TEMPERING OF AT LEAST ONE OF THE FLUIDS

BACKGROUND OF THE INVENTION

The present invention relates to a device for the transfer of substances between two fluids while simultaneously tempering at least one of the two fluids by means of a third fluid, and more particularly, the present invention is mainly intended for use as a so-called blood oxygenator for mixing oxygen or oxygen containing gas into the blood of a patient before returning the blood to the patient.

Prior art blood oxygenators are known in which a patient's blood passes along one side of a semipermeable membrane with an oxygen containing gas passing on the other side thereof so that oxygen bubbles diffuse through the membrane into the blood to achieve an effective oxygenation thereof. In such prior art blood oxygenators, it is also known to temper at least one of the fluids being conducted along one side of the semipermeable membrane. For example, in U.S. Pat. Nos. 3,212,498 and 3,332,746, there are disclosed blood oxygenator apparatus in which blood is conducted between pairs of semipermeable membranes with oxygen and/or dialysis solution arranged to be conducted on the outer surfaces of the semipermeable membrane to result in diffusion of the second fluid into the blood. In each of these apparatus, frame members or apparatus are provided between which the pairs of membranes containing blood are supported and between which flow paths for oxygen and/or dialysis fluid are defined for diffusion of substances through the membranes. The frame apparatus also includes means for tempering of one of the fluids being used in the diffusion process. This tempering in these prior art arrangements has comprised passing a third fluid along one side of a plate member of the frame apparatus with one of the other fluids passing along the other side of the plate member. That is, in each of these prior art references, the tempering fluid is passed along one side of a plate and the oxygen containing fluid or dialysis fluid passed along the opposing side of the plate so that the oxygen containing fluid or dialysis fluid is tempered.

SUMMARY OF THE INVENTION

The present invention provides an improved apparatus for the transfer of substances between two fluids while simultaneously tempering of at least one of the fluids. In accordance with the present invention, the apparatus comprises at least one heat permeable membrane having first and second opposing surfaces for the transfer of heat therethrough. First and second fluid conducting means are provided for conducting a first fluid and a second fluid, and transfer means are provided for transferring substances between the first and second fluids. The second fluid conducting means conducts the second fluid along the first surface of the heat permeable membrane, and third fluid conducting means are provided for conducting a third fluid along the second surface of the membrane for tempering of the second fluid.

Accordingly, with such an apparatus, it is possible to obtain a very compact construction of the apparatus, and in particular to provide a simplified structure for transferring heat from a tempering fluid to another fluid being used in the transfer substances between two fluids. In particular, the use of a heat permeable membrane as opposed to the use of a plate and frame members of the prior art results in a significant advantage in achieving a compact construction for the apparatus and simplification of manufacture of the component parts thereof, such as for example by injection molding and mass production, thereby resulting in a less expensive contruction which can be discarded after use. This latter point is very important in view of the hygiene of the patient being treated as well as for the personnel treating the person.

According to a preferred embodiment of the present invention, a pair of heat permeable membranes are provided with the first surfaces thereof arranged to oppose one another and the third fluid conducting means conducts a third fluid between the membranes of the pair. According to a further preferred embodiment of the present invention, the second fluid conducting means comprise spacing plates having flow channels therein, the spacing plates being arranged in juxtaposition with the second surfaces of the heat permeable membrane. In a preferred form, a plurality of pairs of heat permeable membranes and pluralities of spacing plates are provided, with the spacing plates being arranged in a stack with pairs of heat permeable membranes position therebetween to provide a compact construction.

In another preferred embodiment, the transfer means for transferring the substances between the first and second fluids comprises means for directly mixing of the first fluid into the second fluid, the direct mixing means being located upstream of the heat permeable membrane. According to another preferred embodiment of the present invention, the transfer means comprises a semipermeable membrane for transferring the substances between the first and second fluids by the process of diffusion, the first fluid conducting means conducting the first fluid along one surface of the semipermeable membrane with the other surface of the semipermeable membrane being in contact with the second fluid.

In a still further preferred embodiment, pairs of semipermeable membranes are provided with the first fluid being conducted between the membranes of the pairs. Preferably, these pairs of semipermeable membranes are arranged between pairs of spacing plates, the spacing plates thus being juxtaposed between a pair of semipermeable membranes and a pair of heat permeable membranes.

These and further features and characteristics of the present invention will be apparent from the following detailed description in which reference is made to the enclosed drawings which illustrate the preferred embodiment of the present invention.

BRIEF DESCRIPTION OF THE DRAWINGS

FIG. 2 shows relatively schematically a sectional view of the second preferred embodiment of the apparatus in accordance with the present invention;

FIG. 3 is an elevational view of the apparatus shown in FIG. 2 as viewed from the left-hand side;

FIG. 4 is a top cross-sectional view of the apparatus shown in FIG. 2;

FIG. 5 is an elevational view of the apparatus shown in FIG. 2 as viewed from the right-hand side;

FIG. 6 is an elevational view of the apparatus shown in FIG. 2 as seen in the direction against the plane of the drawing according to FIG. 2;

FIG. 7 is a cross-sectional view taken along lines VII—VII of FIG. 6;

FIGS. 8 and 9 show two elevational plan views of the opposite sides of a spacing plate useful in accordance with the apparatus of the present invention, a number of such spacing plates being used in the apparatus as shown in FIGS. 2-6;

FIG. 10 shows a sectional view taken along lines X—X of FIG. 9;

FIG. 11 shows a sectional view taken along lines XI—XI of FIG. 9;

FIG. 12 shows a sectional view taken along lines XII—XII of FIG. 8;

FIG. 13 shows a sectional view taken along lines XIII—XIII FIG. 9;

DETAILED DESCRIPTION OF THE PREFERRED EMBODIMENT

The term fluid, in the foregoing as well as in the following, relates to gases as well as to liquids. Furthermore, as the apparatus in accordance with the present invention is intended mainly for use as a so-called blood oxygenator, the description for the present invention will be made with reference to such apparatus. However, it will be clear to those versed in the art that the apparatus can also be used in other cases where it is desired to transfer substances between two fluids with a simultaneous tempering of one of the fluids, such as for example, in connection with dialysis.

Figure 1:
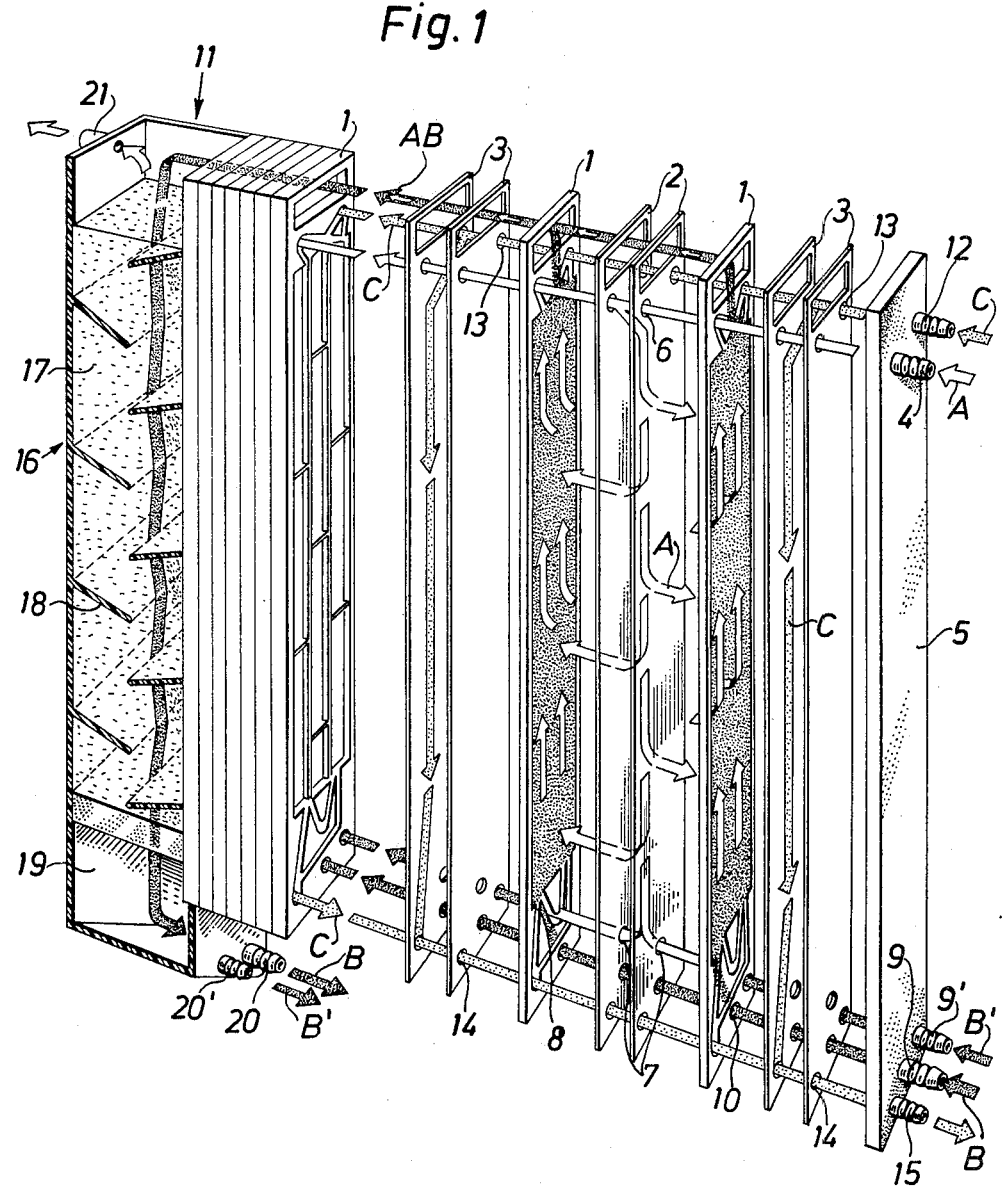
FIG. 1 shows relatively schematically an exploded view of a first embodiment of the apparatus in accordance with the present invention.

Referring now to FIG. 1, the apparatus in accordance with the present invention is comprised of a number of spacing disks or plates 1, provided with flow channels and with pairs of membranes 2,2 and 3,3 respectively, arranged between the spacing plates 1. The membranes 2 comprise semipermeable membranes which are adapted so as to allow a first fluid (i.e., a gas containing oxygen when the present invention is to be used as a oxygenator) to pass through the membrane in the form of microscopic bubbles. This first fluid may for example consist of air, oxygen, or some other oxygen mixture useful in oxygenating a second fluid, namely, blood.

The path of the gas is indicated in FIG. 1 by the arrows marked A. Accordingly, the gas is supplied through a connecting nozzle 4 in an end plate 5, and is conducted to a pair of membranes 2,2 to be subsequently introduced between them downwardly therethrough. For this purpose, the membranes 2 are provided at their upper ends with appropriate apertures 6 through which the gas is introduced between the membranes 2. At the lower ends of the membranes 2, apertures 7 are provided for conducting the gas out of the membranes 2. With the help of channels 8 provided in the spacing plates 1, the gas is conducted out of the membranes and is mixed directly into the second fluid, namely blood, being conducted on the opposite sides of the membranes 2.

The path of blood has been indicated in FIG. 1 by arrows marked B. Accordingly, the blood is introduced into the device through a connecting nozzle 9 provided in the end plate 5 and is conducted to apertures 10 provided in the lower ends of the spacing plates or disks 1. From these apertures 10, the blood is conducted further to the active part of the spacing discs or plates 1 via flow channels in the manner as described more fully in connection with the second embodiment of the subject invention described in the following. In the spacing plates 1, the blood is mixed with the gas which is diffused through the membranes and which is introduced through the channels 8. The blood is then discharged in the direction indicated by the arrow AB to the skimming section which is designated as a whole by the reference numeral 11. The arrow B' and the connecting nozzle 9' indicate an extra blood intake into the device which can be used in connection with special operations, such as for example coronary perfusion.

The arrow C shown in FIG. 1 indicates the path of a tempering fluid, for example water, which is supplied to and withdrawn from the device. This water is tempered either for cooling or for heating of the blood. As seen in FIG. 1, the water is introduced through a connecting nozzle 12 in the end plate 5. From there, the water is conducted by apertures 13 into the space between membranes 3,3 which are preferably heat permeable. In the membranes 3,3 the water is conducted downwardly through the device and serves to temper the blood being conducted in the channels of the spacing plate 1 arranged along the opposite outer surfaces of the membranes 3,3. The water is then withdrawn from the membranes in the device via apertures 14 and a connecting nozzle 15 in the end plate 5.

The skimming section 11 in the example shown consists of a substantially vertical shaft 16 which is filled with polyurethane foam 17 and with pores between inclined plates 18. At the bottom of the shaft 16 is connected a reservoir 19 with two outlets 20, 20' corresponding to the inlets 9, 9', respectively. Finally, numeral 21 designates an outlet for the skimmed off gas.

Thus, it is seen that in accordance with the apparatus of the present invention, the tempering fluid (i.e., the water) is conducted along one surface of a heat permeable membrane 3 with the second fluid (i.e., blood) being conducted along the other surface of the membrane 3 for the simultaneous tempering thereof. In the embodiment shown in FIG. 1, the blood is also oxygenated by conducting the first fluid (i.e., the oxygen containing gas) along one surface of a semipermeable membrane 2 which is permeable to oxygen with the other surface of the semipermeable membrane 2 being in contact with the blood.

Such an arrangement in which the tempering fluid and the fluid to be tempered (i.e., the blood) are separated by a heat permeable membrane 3 is advantageous in providing a very compact yet efficient construction especially if component parts such as generally used in the construction of dialyzers are employed. Such component parts can be manufactured for example, by injection moulding and/or mass production, thereby resulting in a less expensive construction which may be discarded after use. This latter point is particularly important in view of the hygiene of the patient being treated as well as for the personnel treating the patient.

It is further to be noted that this arrangement of the apparatus in which the first and third fluids (i.e., the gas containing oxygen and the tempering fluid, respectively) are conducted between pairs of membranes 2,2 and 3,3 arranged plane parallel to one another is similar to that used in connection with artificial kidneys of the plate type. It will be clear however to those versed in the arts that other basic constructions such as are used in artificial kidneys and dialyzers may also be used. For example, the membranes may be helically wound or may comprise tubular fibers as in other types of dialyzers.

In this regard, it should be further noted that as in dialyzers, the spacing elements or plates 1 in the form of disks having flow channels or the like are arranged in the apparatus between pairs of membranes 2,2 and 3,3. These spacing plates 1 are preferably adapted so that they conduct the second fluid, that is the blood, along the outside of the membranes in the pairs of membranes 2,2 and 3,3 and preferably in a counter flow in relation to the first fluid and the third fluid being conducted through the pairs of membranes 2,2 and 3,3. Thus, the oxygen containing gas and the tempering fluid are both conducted in the form of thin layers between the respective membranes 2,2 and 3,3 on either side of a thin blood layer in the spacing plates 1 provided with channels. In this respect, it is to be noted that the construction in accordance with the present invention thus differs from dialyzers which usually conduct the blood enclosed between two membranes or in tubes or fibers of membrane material.

Still further, it is to be noted that the third fluid for tempering of the blood is appropriately separated from the gas mixture by placing the tempering membranes 3,3 along the sides of the spacing elements 1 remote from the semipermeable membranes 2,2. This third fluid may either comprise a gas or a liquid which is intended for the heating or other tempering of the blood, and is preferably suitably arranged to conduct a third fluid in counter flow with respect to the blood.

The skimming section 11 has been provided for eliminating an excess of oxygen supplied and mixed into the blood before the blood is returned to the patient, which excess of oxygen is supplied in order to achieve an effective oxygenation of the blood.

Turning now to FIGS. 2-21, there is shown in greater detail a further embodiment of the apparatus in accordance with the present invention. For the parts corresponding to those of the construction illustrated in FIG. 1, the same reference designations have been used, but with the addition of an "a". As best seen in FIGS. 2-4, the construction of this further preferred embodiment comprises a number of spacing plates or disks 1a with pairs of membranes 2a and 3a respectively arranged between them. The spacing plate and membrane packet is held together by a clamping plate or end plate 5a which, with the help of clamping bars 22 is maintained pressed against a skimming unit 11a, the one end wall 23 of which has substantially the same shape as the clamping plate 5a. Blood is introduced via an inlet 9a which is shown in greater detail in FIGS. 20 and 21 described hereinbelow. In a similar manner, gas is introduced through an inlet 4a which is shown in greater detail in FIGS. 18 and 19, also discussed more fully hereinbelow.

The actual oxygenating and heating part of the device as a whole has been designated generally by numeral 24. The oxygenated blood leaves this section 24 via an outlet 25 and flows via a funnel 26 downwardly into a vertical shaft 27 which is formed by rings 28 and a base 29 of polyurethane foam or similar material with open pores therein. The skimmed off blood then drains into a collecting reservoir 30 and can be discharged via any of five different outlets 31, 32, 33, 34, and 35. The outlets 33, 34 and 35 are intended for connection to gauges for the measurement of pressure and temperature and for the taking of samples respectively. The actual main outlet for the blood to be returned to the patient is designated 32. Numeral 31 designates the special outlet which is intended for use in connection with, for example, coronary perfusion. Reference numeral 36 designates an outlet for skimmed off gas. This outlet 36 is preferably covered with a cap 37. Further, reference numerals 38 and 39 designate two inlets which may be utilized for the supply of different media, for example, heparin, etc.

As with the embodiment shown in FIG. 1, the main active portion of the apparatus 24 is comprised of a plurality of spacing plates or disks 1a provided with flow channels for conducting blood therein and with elongated membranes 2a, 3a, arranged in pairs for the gas mixture and for the heating medium, respectively, between the spacing plates 1a. Preferably, the membranes 2a for the gas mixture alternate with the membranes 3a for the heating medium between the spacing plates 1a.

The construction of the spacing plates 1a can best be seen in FIGS. 8-13. The blood inlet is designated in these figures generally by numeral 40. From this inlet 40, the blood flows first through channels designated 41 on one side of the plate 1a (see FIG. 8) to continue subsequently through the plate 1a via relatively small holes 42 and then further through ducts or channels 44, 45, 46, and 47 on the other side of the plate 1a (see FIG. 9) to the truly active portion or part of the plate 1a which is designated generally 48. This active part 48 of the plate 1a comprises transverse bars 49 which uphold longitudinal compression strips 50. Between the compression strips 50, the bars 49 uphold supporting strips 51 which alternatively face the two sides of the plate 1a, but which are somewhat retracted in relation to the outer surfaces of the compression strip 50. The oxygenated blood is subsequently removed via channels 52, 53, and 54 (see FIG. 9), through smaller holes 55 which extend through the plate 1a and further on the other side of the plate 1a (see FIG. 8) through channels 56 to an outlet opening 57.

Reference numerals 58, 59, and 60 designate different sealing beads which are shown most clearly in FIG. 10. These sealing beads 58, 59, and 60, with the help of special packings 75 (shown in more detail in FIG. 15) which press the adjacent membranes 2a, 3a against the sealing beads 58, 59 effectively seal the flow of blood from the other flow of gas and/or tempering fluid.

The gas and the tempering water are introduced via openings 61, 62 respectively and from there are further conducted between the membranes 2a, 2a or 3a, 3a with the help of special "buttons" which will be described in more detail hereinbelow in connection wit FIGS. 14–16. The gas, after conduction along the surface of the membranes 2a, 2a is then introduced into the blood via apertures 63 in the membranes 2a, as most clearly shown in FIG. 17. These membranes 2a, 3a are provided moreover with further apertures 61', 62', 57', 40', and 64' corresponding to the holes 61, 62, 57, 40 and 64 respectively in the plate 1a. In this regard, it is appropriate here to compare FIG. 17 with FIG. 9. Reference numeral 64 designates the outlet for the water or the tempering fluid. Special buttons are also provided here, too, between the membranes, as more fully described in detail hereinbelow in connection with FIGS. 14–16.

Reference numerals 65 and 66 in FIG. 11, and 67 and 68 in FIG. 13, designate sealing beads which are intended to cooperate with the aforementioned buttons. In the same manner, the sealing beads 69 and 70 shown in FIG. 13 are intended to cooperate with the special packings 75.

FIG. 5 shows the apparatus in accordance with FIG. 2 as seen from the right. Numeral 4a designates the inlet for the gas mixture and 12a the water or tempering fluid intake. In the same manner, 9a designates the blood inlet and 15a the water discharge. For the rest, FIG. 5 illustrates essentially only the clamping plate 5a. In addition, however, the positions of the section lines XIV—XIV, XV—XV, and XVI—XVI are shown which correspond to the sections shown in more detail in FIGS. 14–16.

FIG. 6 illustrates the oxygenating section proper of the apparatus in accordance with the present invention, which as a whole is designated 24. This section is attached to the skimming section 11a with the help of clamping plates 5a and clamping bars 22.

FIG. 7 shows a section taken along lines VII—VII of FIG. 6. Numeral 25 designates the outlet for the oxygenated blood. The skimming section 11a is situated partly concealed behind its end wall 23 which has the same function as the clamping plate 5a—namely, tightly clamping together the plates 1a with the membranes 2a, 3a arranged therebetween.

Figure 14:
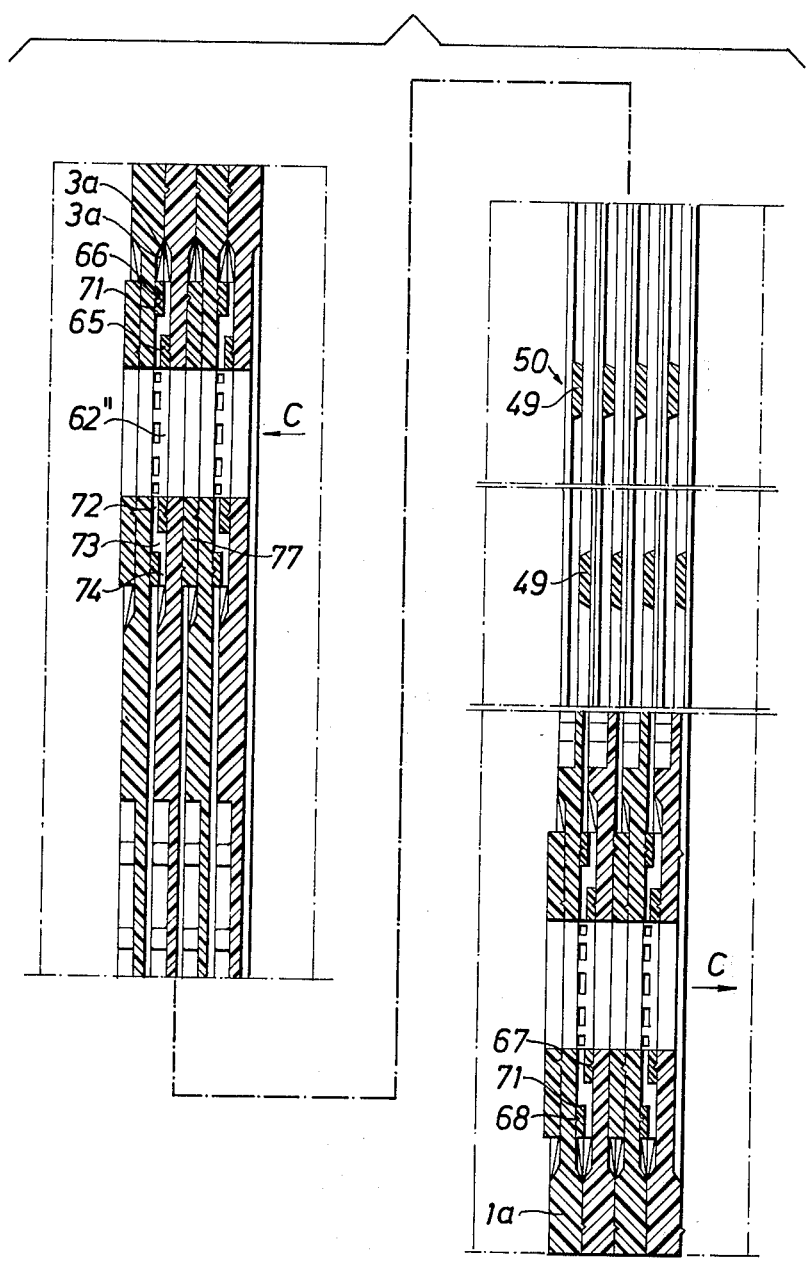
FIG. 14 shows a sectional view taken along lines XIV—XIV of FIG. 5.

FIG. 14 shows in greater detail how the water is introduced between the membranes 3a, 3a, how it is conducted therealong, and subsequently how it is removed from these membranes 3a, 3a with the help of special sealing buttons 71. These sealing buttons 71 which are placed between the membranes 3a, 3a each have a central opening 62" from which the water is conducted through the channel 72 on one side of the button, through holes 73 extending through the buttons and then through channels 74 on the other side of the buttons 71. The buttons 71 are adapted so as to seal against the sealing beads which are identical with the sealing beads 65 and 66 shown in FIG. 11, but which surround the aperture 62. At the outlet end of the apparatus, similar and corresponding sealing buttons 71 are provided which press instead against the sealing beads 67, 68 on plate 1a as shown in FIG. 13, to form a seal so that the tempering fluid will be conducted through the outlet holes 64.

Figure 15:
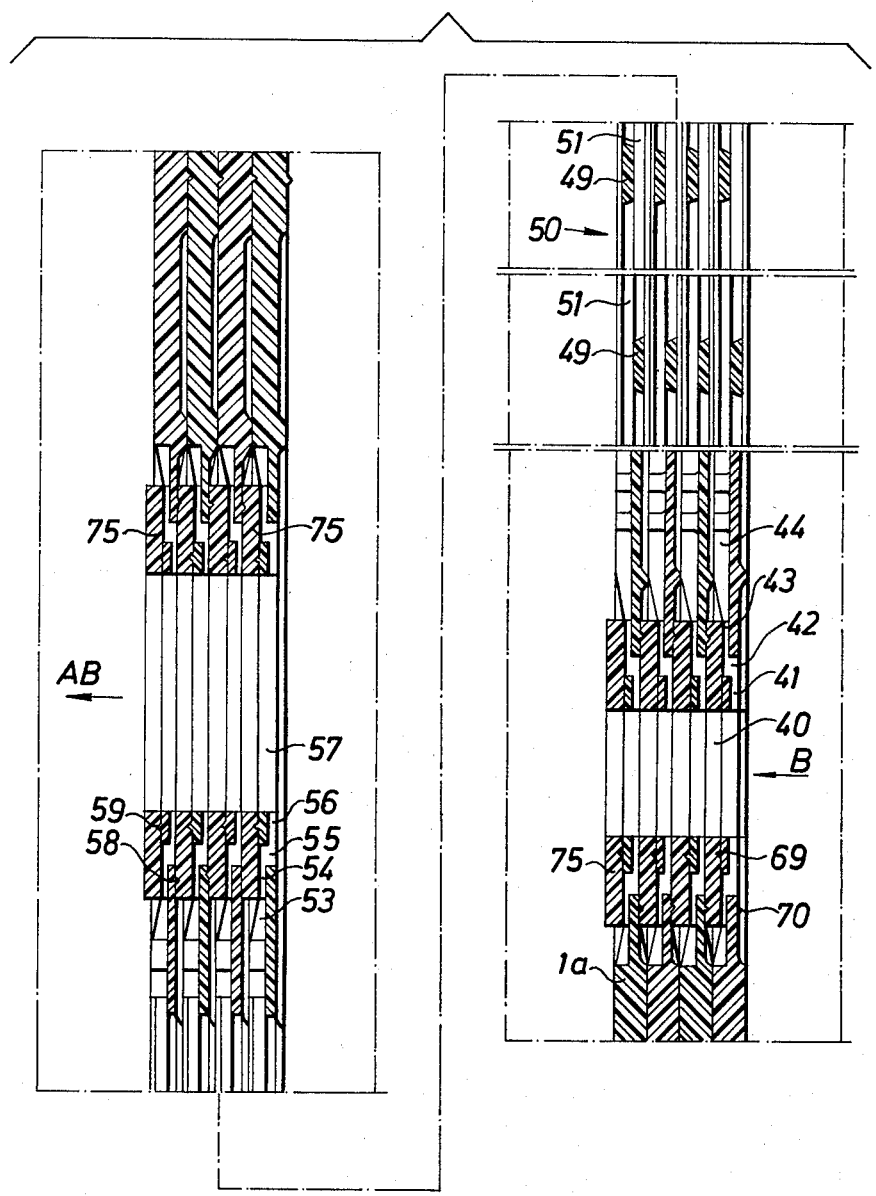
FIG. 15 shows a sectional view taken along lines XV—XV of FIG. 5.

In FIG. 15, there is shown how the blood is introduced at the place indicated by the arrow B and discharged in oxygenated state state at the place indicated by the arrow AB. The apertures and channels 40, 41, 42, 43, and 44 at the inlet end and the apertures and channels 53, 54, 55, 56, and 57 at the outlet end have previously been described with reference to FIGS. 8 and 9. With the help of sealing beads 69 and 70 at the inlet end, and 58 and 59 at the outlet end, the blood flow is effectively sealed off against the other flows of gas and water with the help of packings 75.

Figure 16:
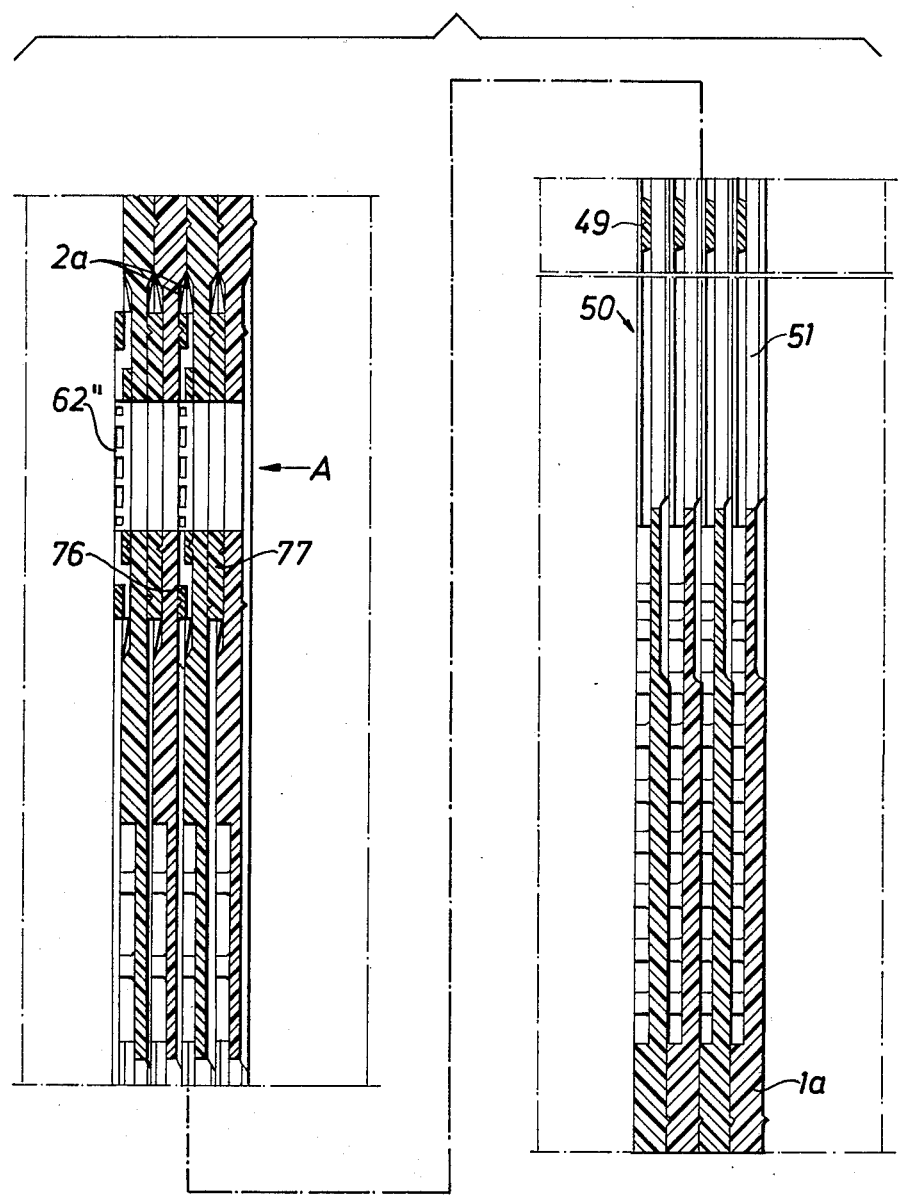
FIG. 16 shows a sectional view taken along lines XVI—XVI of FIG. 5.
Figure 17:
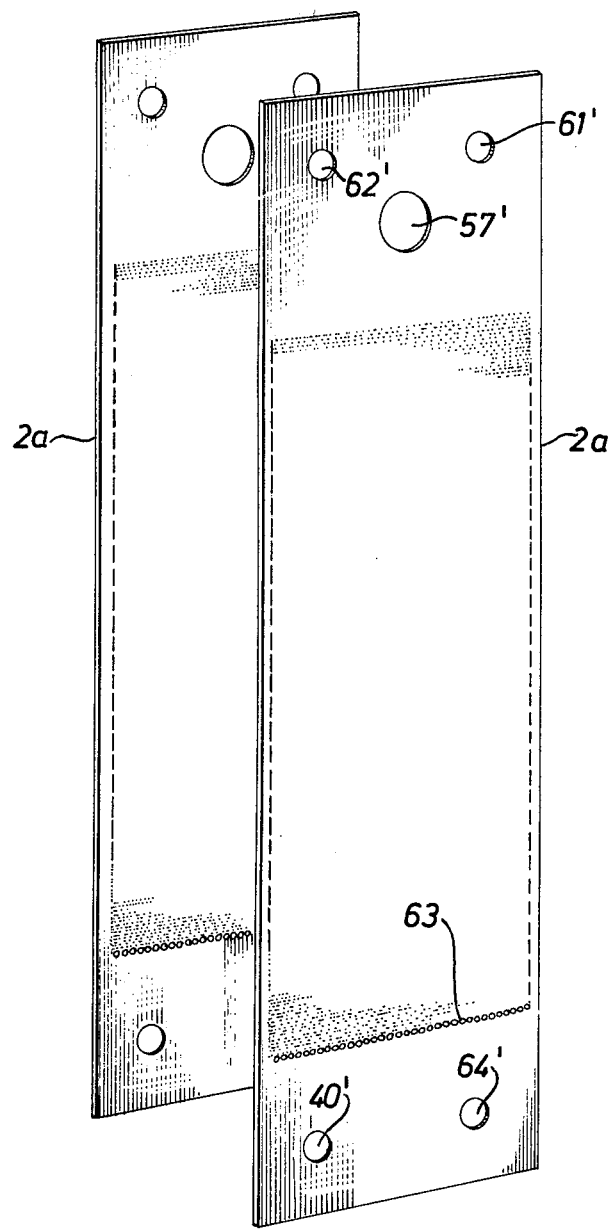
FIG. 17 shows a perspective view of two membranes, a number of which are intended to be arranged in pairs between the spacing plates of the type shown in FIGS. 8-13.

In FIG. 16, there is shown how the gas is introduced at the place indicated by the arrow A and is then conducted downwardly between the membranes 2a, 2a with the help of special sealing buttons 76. These sealing buttons 76 are substantially identical with the sealing buttons 71 described hereinabove with reference to the conduction of the tempering fluid and therefore need not be described in detail here. The gas mixture is conducted from the membranes 2a and into the blood flow partially by direct diffusion through the membrane 2a, and partially through a series of holes 63 provided at the lower ends of the membranes 2a, 2a, shown most clearly in FIG. 17. This series of small holes 63 preferably have a diameter of the order of magnitude of 50 microns which thus produces a high pressure drop and consequently an even distribution of the gas mixture.

With respect to the aforementioned diffusion of the gas mixture into the blood, it is preferable that the membranes 2a be microporous with pores or holes on the order of magnitude of 0.02 microns and of a thickness of approximately 20–25 microns. Examples of such membranes are various stretched PE or PP membranes, or expanded teflon membranes. Alternatively, various silicone membranes may be used which are not microporous in the true meaning of the word but wherein the diffusion takes place through the membrane material itself.

Reference numeral 77 designates "blind buttons" which are intended to be introduced into the membrane layers where a particular fluid is undesirable. In this manner, the gas mixture can be conducted through the pair of membranes 3a, 3a intended for the tempering water without being mixed with the tempering water or being conducted between the pair of membranes 3a, 3a. In a similar manner, the water or tempering fluid can be conducted through the pair of membranes 2a, 2a intended only for the gas without being mixed with the gas or flowing into the space between the membranes 2a, 2a.

In FIGS. 14–16, there is shown again the transverse bars 49, the longitudinal compression strips 50, and the supporting strips 51. The truly active surface of the spacer plates 1a however has not been shown.

Figure 18:
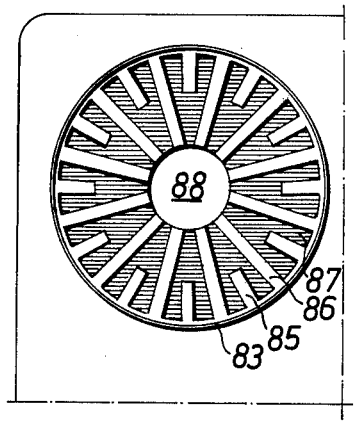
FIGS. 18 and 19 show on a larger scale a detail of the portion of the apparatus shown in FIG. 2 found within the circle designation XVIII—XIX.
Figure 19:
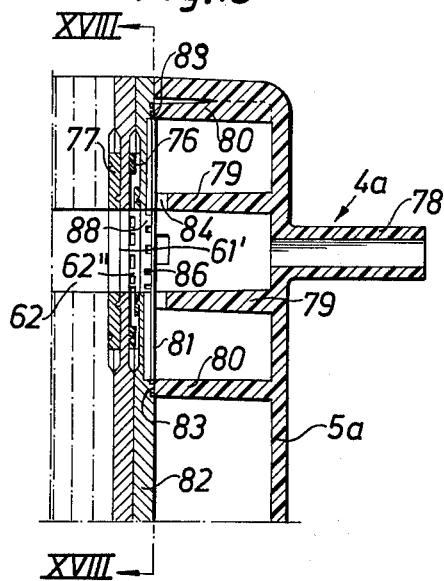

Referring now to FIGS. 18 and 19, which show on a larger scale the detail of FIG. 2 found within the circle designated XVIII-XIX, there is shown a gas inlet 4a for introduction of the gas mixture via a gas nozzle 78 which is preferably moulded onto the end plate or clamping plate 5a. With the aid of two inner concentric nozzles 79, 80, a filter 81 is pressed against an outer end plate 82. The sealing bead 83 provides an effective seal between the end plate 82 and the clamping plate 5a. With the help of channels 84, the gas mixture is guided over the entire surface of the filter 81. After filtration, the gas is conducted through the channel 62 formed by apertures 61' and 62". Examples of usable filters are sintered PE or PP materials of a thickness of approximately 20 microns and a pore size of approximately 0.2–0.5 microns. Alternatively, a glass fiber material could be used.

FIG. 18 shows a section along lines XVIII—XVIII of FIG. 19 and thus shows the supporting surface proper for the filter 81. This supporting surface, which is thus located inside the sealing bead 83, is formed by radially arranged supporting strips 85 and 86 with channels in between which open out into a central opening 88.

Figure 20:
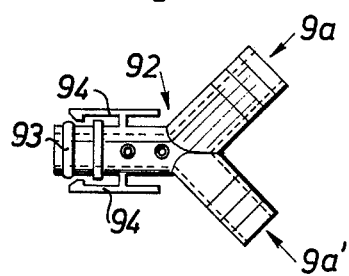
FIGS. 20 and 21 show on a larger scale a detail of the portion of the apparatus shown in FIG. 2 found within the circle designation by XX—XXI.
Figure 21:
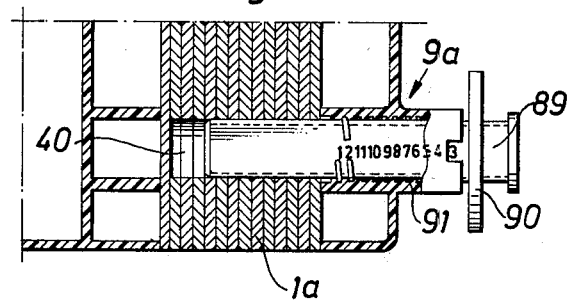

FIGS. 20 and 21 show schematically how the blood inlet 9a can be adapted for the setting of different capacities so that the same apparatus can be used for both adults as well as children. The inlet for the blood comprises a tubular plunger 89 which, with the help of a handwheel 90 and a thread 91, can be adjusted to different depths in the shaft or flow passage 40 formed by the apertures in the spacing plates 1a. The outer surface of the plunger 89 thus serves as a shut-off element for the flow channels 41 of those spacing disks 1a with which the plunger 89 is in blocking alignment. That is, the outer surface of the plunger 89 serves to close off to prevent the flow of blood to certain numbers of the spacing disks 1a, depending upon its depth into the shaft formed by the apertures 40 in the disks 1a. In the example shown, the device is set for treatment with three spacer disks 1a, and thus only the flow channels 41 of three of the spacer disks 1a are opened to receive blood introduced into the plunger 89. The remaining spacer disks are closed off by the outer surface of the plunger 89 to prevent the flow of blood therethrough. The capacity of the device can be increased fourfold in the embodiment shown by withdrawing the plunger 89 to its full extent to open the flow channels in all of the spacing disks 1a.

To the plunger 89, there is preferably connected a Y-coupling with two inlets 9a and 9a' corresponding to the inlets 9 and 9' in the construction according to FIG. 1. The seal between the Y-coupling 92 and the plunger 89 is achieved with the help of an O-ring 93 and the actual retention of the Y-coupling 92 is achieved with the help of hooks 94 which engage the enlarged end of the plunger 89.

Figure 22:
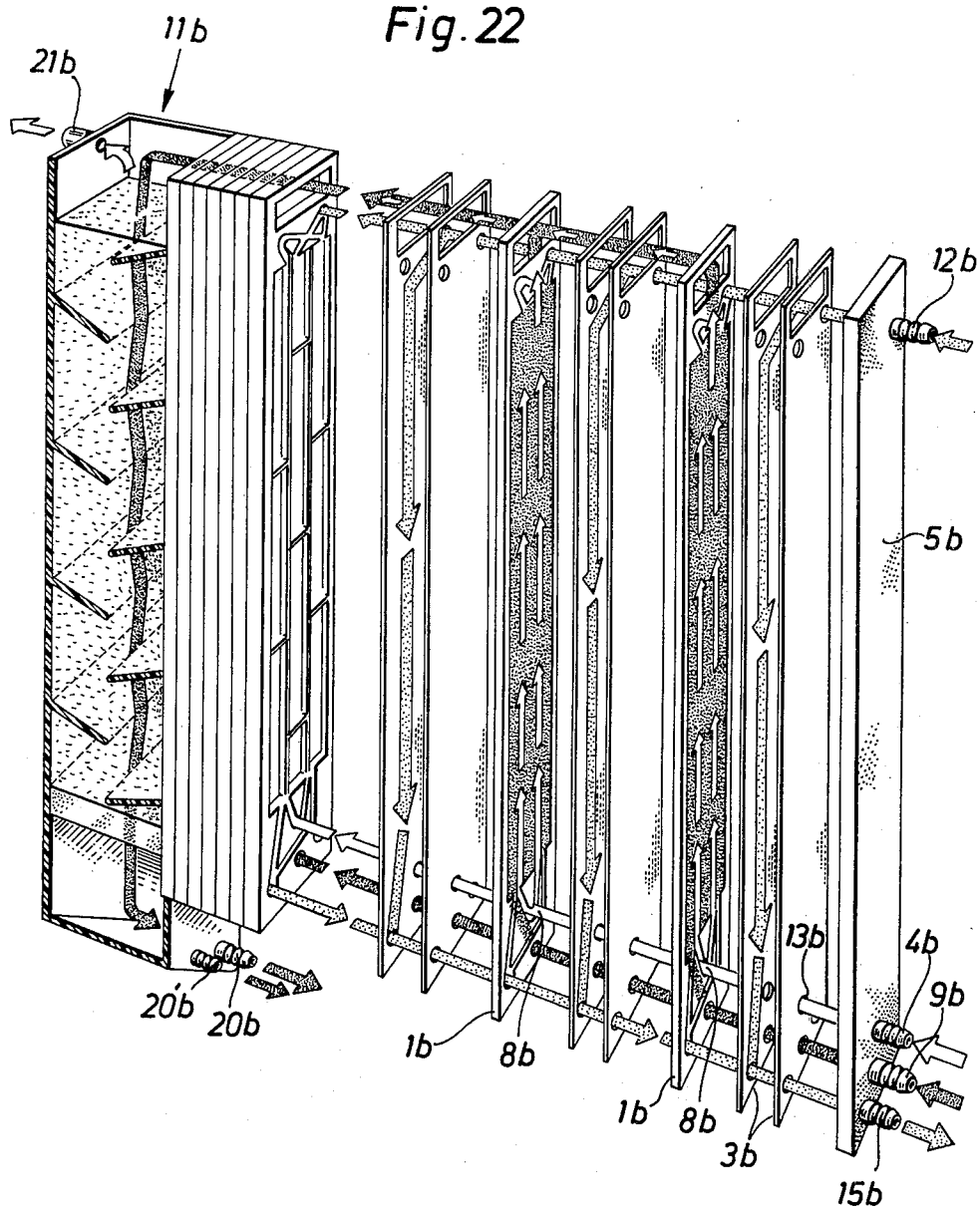
FIG. 22 shows schematically in the same manner as FIG. 1, a third embodiment of the apparatus in accordance with the present invention.

In FIG. 22, there is shown a further embodiment for the apparatus in accordance with the present invention. Since this arrangement substantially corresponds to the construction of FIG. 1, the same reference designations will therefore be used, but with the addition of the letter "b". The difference between the constructions according to FIG. 1 and FIG. 22 consists mainly in that the semipermeable membranes 2 for diffusion of a first fluid (namely, the gas) into the second fluid (i.e., the blood) have been omitted in the latter construction. Instead, a direct mixing of the gas mixture into the blood takes place via inlet 4b in the clamping plate 5b, apertures 13 in the membranes 3b and the channels 8b in the spacer disks 1b. Blood is introduced in the same manner as in the construction according to FIG. 1, namely, through the connecting nozzles 9b. Subsequently, the oxygenated blood is removed by a deaeration unit 11b having an excess air outlet 21b and blood outlet 20b and 20b'. The third fluid, that is to say the tempering fluid which in the preferred embodiment is water, is introduced in the same manner as in the construction according to FIG. 1 via an inlet nozzle 12b and is discharged from the apparatus by an outlet nozzle 15b. Since the construction according to FIG. 22 otherwise largely corresponds to that according to FIG. 1, no further description is required.

The advantage of this construction is that a thin layer of blood can be effectively tempered from two sides at the same time as it is oxygenated with the help of a gas mixture introduced directly into the blood prior to the tempering thereof. In this regard, it is also to be noted that the apparatus in accordance with the present invention can also be used in other cases where it is desirable to provide for a simultaneous tempering of at least one of the fluids used in transferring of substances between two fluids. For example, it may be desired to use the apparatus in connection with dialysis, and should not necessarily be deemed to be limited to use only in connection with blood oxygenation.

While the preferred embodiment of the present invention has been shown and described, it will be understood that such is merely illustrative and that changes may be made without departing from the scope of the invention as claimed. Moreover, reference is made to U.S. patent application Ser. No. 6,248 filed on even date herewith, which presents substantial similarities of construction with that of the present application.

What is claimed is:

1. Apparatus for the transfer of substances between first and second fluids comprising:
   at least one heat permeable membrane having first and second opposing surfaces for the transfer of heat therethrough;
   first fluid conducting means for conducting a first fluid through a portion of said apparatus;
   a plurality of spacing plates arranged in stacked relationship, said spacing plates including flow channels therein for conducting a second fluid therethrough, at least one of said spacing plates being juxtaposed to said first surface of said at least one heat permeable membrane for conducting a portion of said second fluid through said flow channels thereof along said first surface of said heat permeable membrane;
   second fluid introduction means for introducing a second fluid into said flow channels of said spacing plates, said second fluid introduction means including inlet apertures through each of said spacing plates, said inlet apertures being aligned with one another to define a fluid passage through said stack of spacing plates, and said flow channels of said spacing plates being in communication with said inlet apertures in said spacing plates;
   transfer means for transferring substances between said first and second fluids;
   third fluid conducting means for conducting a third fluid along said second surface of said heat permeable membrane for tempering said portion of said second fluid conducted along said first surface; and
   adjustable control means for controlling the introduction of said second fluid to only a predetermined number of spacing plates, said adjustable control means comprising a shut-off element movable to selectively shut off said flow channels of said spacing plates other than said predetermined number of spacing plates so that said second fluid is only introduced into said predetermined number of said spacing plates.

2. The apparatus of claim 1 wherein said shut-off element comprises a tubular plunger adjustably movable within said fluid passage, the outer surface of said tubular plunger being adapted to block said flow channels in alignment therewith.

3. The apparatus of claim 2 wherein said at least one heat permeable membrane comprises a first heat permeable membrane, and further including a second heat permeable membrane having first and second opposing surfaces, said first and second heat permeable membranes being disposed with said second surfaces facing one another; and wherein said third fluid conducting means conducts said third fluid between said first and second heat permeable membranes.

4. The apparatus of claim 3 further including a plurality of said first and second heat permeable membranes arranged in pairs, each pair of said first and second heat permeable membranes being arranged between a pair of said spacing plates; and wherein said third fluid conducting means conducts said third fluid between said first and second heat permeable membranes of said pairs of heat permeable membranes.

5. The apparatus of claim 4 wherein said transfer means comprises at least one semi-permeable membrane having first and second opposing surfaces, said second surface of said semi-permeable membrane being juxtaposed to one of said spacing plates of said plurality of spacing plates and being in contact with said second fluid as said second fluid is conducted through said flow channels of said one spacing plate, said at least one semi-permeable being permeable to a substance in said first fluid to transfer said substance to said second fluid through said at least one semi-permeable membrane, and wherein said first fluid conducting means conducts said first fluid along said first surface of said at least one semi-permeable membrane.

6. The apparatus of claim 5 wherein said at least one semi-permeable membrane comprises a first semi-permeable membrane, and further including a second semi-permeable membrane having first and second opposing surfaces, said first and second semi-permeable membranes being disposed with said first surfaces opposing each other and said second surfaces facing one another between a pair of said spacing plates, and wherein said first fluid conducting means conducts said first fluid between said first and second semi-permeable membranes.

7. The apparatus of claim 6 further including a plurality of said first and second semi-permeable membranes arranged in pairs, each pair of first and second semi-permeable membranes being disposed on one side of each of said spacing plates, and each pair of said first and second heat permeable membranes being disposed on the other side of each of said spacing plates; and wherein said first fluid conducting means conducts said first fluid between said first and second semi-permeable membranes of said pairs of semi-permeable membranes.

8. The apparatus of claim 7 further including means for clamping together said plurality of stacked spacing plates.

9. The apparatus of claim 8 wherein said semipermeable membranes, said heat permeable membranes and said spacing plates each have an inlet end and an outlet end for the respective fluids being conducted therethrough, said inlet ends of said membranes for said first and third fluids being arranged adjacent said outlet ends of said spacing plates, and said outlet ends of said membranes being adjacent said inlet ends of said spacing plates so that said first and third fluids are conducted in counter flow with respect to said second fluid.

10. The apparatus of claim 8 wherein said stacked spacing plates and membranes are adapted to be arranged in a vertical position, and wherein said inlet ends of said membranes are at the upper end of said vertically arranged stack and wherein said inlet ends of said spacing plates is at the lower end of said stack.

11. The apparatus of claim 10 further including filtering means arranged upstream of said semi-permeable membranes for filtering said first fluid prior to said first fluid being introduced between said semi-permeable membranes.

12. The apparatus of claim 11 wherein said first fluid is an oxygen containing gas, and said second fluid is blood to be oxygenated.

13. Apparatus for tempering a first fluid with a second fluid, said apparatus comprising:
a plurality of pairs of heat permeable membranes for transfer of heat therethrough, each of said heat permeable membranes having first and second opposing surfaces, and said heat permeable membranes of each of said pairs of membranes being adjacent to one another and arranged with said second surfaces facing one another and with said first surfaces facing away from one another;
a plurality of spacing plates arranged in stacked relationship with each of said pairs of heat permeable membranes being arranged between a pair of spacing plates so that said first surfaces of said heat permeable membranes are in juxtaposition to one of said spacing plates, said spacing plates including flow channels therein for conducting a first fluid along said first surfaces of said heat permeable membranes in juxtaposition thereto;
first fluid introduction means for introducing a first fluid into said flow channels of said spacing plates, said first fluid introduction means including inlet apertures through each of said spacing plates, said inlet aperures being aligned with one another to define a fluid passage through said stacked spacing plates, said flow channels of said spacing plates being in communication with said inlet apertures in said spacing plates;
second fluid introduction means for introducing a second fluid between said heat permeable membranes of said pairs of heat permeable membranes to temper said first fluid through said heat permeable membranes as said first fluid is conducted through said flow channels along said first surfaces of said heat permeable membranes; and
adjustable control means for controlling the introduction of said first fluid to only a predetermined number of said spacing plates, said adjustable control means comprising a shut-off element movable to selectively shut off said flow channels of said spacing plates other than said predetermined number of spacing plates so that said first fluid is only introduced into said predetermined number of said spacing plates.

14. The apparatus of claim 13 wherein said shut-off element comprises a tubular plunger adjustably movable within said fluid passage, the outer surface of said tubular plunger being adapted to block said flow channels in alignment therewith.

15. The apparatus of claim 13 further including means for clamping together said stacked spacing plates.

16. The apparatus of claim 13 wherein said plurality of spacing plates and said plurality of heat permeable membranes are disposed in a vertical orientation.

17. The apparatus of claim 13 wherein said first fluid is blood.

18. Apparatus for the transfer of substances between first and second fluids comprising:
a plurality of pairs of semi-permeable membranes, each of said semi-permeable membranes having first and second opposing surfaces, and said semi-permeable membranes of each of said pairs of semi-permeable membranes being adjacent to one another and arranged with said second surfaces facing one another and with said first surfaces facing away from one another;

a plurality of spacing plates arranged in stacked relationship with each of said pairs of semi-permeable membranes being arranged between a pair of spacing plates so that said first surfaces of each of said semi-permeable membranes are in juxtaposition to one of said spacing plates, said spacing plates including flow channels therein for conducting a first fluid along said first surfaces of said semi-permeable membranes in juxtaposition thereto;

first fluid introduction means for introducing a first fluid into said flow channels of said spacing plates, said first fluid introduction means including inlet apertures through each of said spacing plates, said inlet apertures being aligned with one another to define a fluid passage through said stacked spacing plates, and said flow channels of said spacing plates being in communication with said inlet apertures in said spacing plates;

second fluid introduction means for introducing a second fluid between said semi-permeable membranes of said pairs of semi-permeable membranes to flow along said second surfaces of said semi-permeable membranes to transfer substances between said first fluid and said second fluid across said semi-permeable membranes as said first fluid is conducted through said flow channels along said first surfaces of said semi-permeable membranes; and adjustable control means for controlling the introduction of said first fluid to only a predetermined number of said spacing plates, said adjustable control means comprising a shut-off element movable to selectively shut off said flow channels of said spacing plates other than said predetermined number of spacing plates so that said first fluid is only introduced into said predetermined number of said spacing plates.

19. The apparatus of claim 18 wherein said shut-off element comprises a tubular plunger adjustably movable within said fluid passage, the outer surface of said tubular plunger being adapted to block said flow channels in alignment therewith.

20. The apparatus of claim 18 further including at least one aperture in said semi-permeable membranes for directly mixing said second fluid into said first fluid through said at least one aperture.

21. The apparatus of claim 18 further including means for clamping together said stacked spacing plates.

22. The apparatus of claim 18 wherein said plurality of spacing plates and said plurality of semi-permeable membranes are disposed in a vertical orientation.

23. The apparatus of claim 18 further including filtering means arranged upstream of said semi-permeable membranes for filtering said second fluid prior to said second fluid being introduced between said semi-permeable membranes for transferring substances between said first and second fluids.

24. The apparatus of claim 18 wherein said first fluid is blood to be oxygenated and said second fluid is an oxygen containing gas.

* * * * *